(12) United States Patent
Oyaizu et al.

(10) Patent No.: US 12,051,807 B2
(45) Date of Patent: Jul. 30, 2024

(54) ELECTRODE MATERIAL

(71) Applicants: WASEDA UNIVERSITY, Tokyo (JP); NISSAN CHEMICAL CORPORATION, Tokyo (JP)

(72) Inventors: Kenichi Oyaizu, Tokyo (JP); Kan Hatakeyama, Tokyo (JP); Tomoki Akahane, Tokyo (JP); Choitsu Go, Tokyo (JP); Takahiro Kaseyama, Funabashi (JP)

(73) Assignees: WASEDA UNIVERSITY, Tokyo (JP); NISSAN CHEMICAL CORPORATION, Tokyo (JP)

( * ) Notice: Subject to any disclaimer, the term of this patent is extended or adjusted under 35 U.S.C. 154(b) by 198 days.

(21) Appl. No.: 17/780,718

(22) PCT Filed: Nov. 24, 2020

(86) PCT No.: PCT/JP2020/043579
§ 371 (c)(1),
(2) Date: May 27, 2022

(87) PCT Pub. No.: WO2021/106834
PCT Pub. Date: Jun. 3, 2021

(65) Prior Publication Data
US 2023/0026457 A1    Jan. 26, 2023

(30) Foreign Application Priority Data
Nov. 29, 2019 (JP) .................................. 2019-216361

(51) Int. Cl.
*H01M 4/60* (2006.01)
*C08F 132/08* (2006.01)
(Continued)

(52) U.S. Cl.
CPC .......... *H01M 4/608* (2013.01); *C08F 132/08* (2013.01); *H01M 4/364* (2013.01);
(Continued)

(58) Field of Classification Search
CPC .... H01M 4/608; H01M 4/364; H01M 4/5825; H01M 4/623; H01M 4/625;
(Continued)

(56) References Cited

U.S. PATENT DOCUMENTS 3,563,917 A * 2/1971 Marvel .............. C08G 73/0694
544/356
2002/0195591 A1 12/2002 Ravet et al.
(Continued)

FOREIGN PATENT DOCUMENTS

JP 2001-15111 A 1/2001
JP 2017-71714 A 4/2017

OTHER PUBLICATIONS

International Search Report (PCT/ISA/210) issued in PCT/JP2020/043579, dated Dec. 28, 2020.
(Continued)

*Primary Examiner* — Andrew J. Oyer
(74) *Attorney, Agent, or Firm* — Birch, Stewart, Kolasch & Birch, LLP

(57) ABSTRACT

Provided is an electrode material which is suitable for use as a material for forming electrodes for use in lithium ion secondary batteries, etc. and which makes it possible to heighten the rate characteristics of batteries. The electrode material is characterized by comprising a polymer having, in a side chain, a fluoflavin skeleton such as that shown by the formula and an inorganic active material, the polymer being contained in an amount of 1 mass % or less with respect to the solid components.

(Continued)

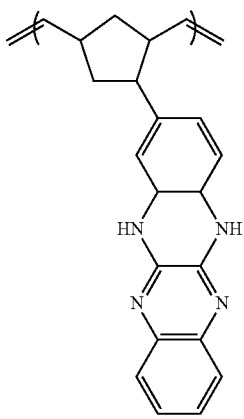

(51) Int. Cl.
*H01M 4/36* (2006.01)
*H01M 4/58* (2010.01)
*H01M 4/62* (2006.01)
*H01M 10/0525* (2010.01)

(52) U.S. Cl.
CPC ......... *H01M 4/5825* (2013.01); *H01M 4/623* (2013.01); *H01M 4/625* (2013.01); *H01M 10/0525* (2013.01)

(58) Field of Classification Search
CPC .. H01M 10/0525; C08F 132/08; Y02E 60/10; C07D 487/04; C08G 61/08; C08G 65/22
See application file for complete search history.

(56) References Cited

U.S. PATENT DOCUMENTS

2017/0014544 A1\* 1/2017 Coqueret .................. C08J 5/18
2017/0104214 A1\* 4/2017 Nishide ................. C08K 3/046

OTHER PUBLICATIONS

Kishida et al., "Synthesis of Polyfluoflavine Derivatives and Application to an Organic Electrode-Active Material," Proceedings of the 95th Annual Meeting of the Chemical Society of Japan, Mar. 11, 2015, p. 741 (total 4 pages).
Written Opinion of the International Searching Authority (PCT/ISA/237) issued in PCT/JP2020/043579, dated Dec. 28, 2020.

\* cited by examiner

14 Claims, 1 Drawing Sheet

ELECTRODE MATERIAL

TECHNICAL FIELD

The present invention relates to an electrode material containing a polymer having a fluoflavine skeleton in a side chain.

BACKGROUND ART

In recent years, downsizing and weight reduction of electronic devices have been promoted, and downsizing and weight reduction of batteries serving as power sources for the electronic devices have also been required. Nonaqueous electrolyte secondary batteries such as lithium ion batteries have been put into practical use as batteries which are downsized, weight-reduced, and chargeable and dischargeable, and have a high capacity, and have been used in portable electronic devices such as small video cameras, mobile phones, and notebook computers, and communication devices and the like.

The lithium ion secondary battery has a high energy density, and has excellent advantages such as a higher capacity and operating voltage than those of other batteries. However, the high energy density may cause a risk of overheating or an accident such as fire depending on the usage condition, and high safety is required for the lithium ion secondary battery. In particular, since a higher energy density and output characteristics are required for hybrid vehicles which have recently been in the spotlight, much higher safety is required for the lithium ion secondary battery.

In general, a lithium ion secondary battery is composed of a positive electrode, a negative electrode, and an electrolyte. During the charge, lithium ions are discharged from a positive electrode active material into the electrolyte, and are intercalated into a negative electrode active material such as carbon particles. During the discharge, lithium ions are discharged from a negative electrode active material into the electrolyte, and are intercalated into a positive electrode active material, whereby a current can be taken out to an external circuit. As described above, in the lithium ion secondary battery, the lithium ions move back and forth between the positive electrode and the negative electrode via the electrolyte, whereby charge and discharge are performed.

Meanwhile, as the performance of portable electronic devices and the like is improved, batteries having a higher capacity are required. Sn and Si and the like, which have a capacity per unit weight much higher than that of existing carbon, have been actively studied as a negative electrode active material. However, when Si or a Si alloy is used as the negative electrode active material, volume expansion increases, which disadvantageously causes deteriorated cycle characteristics. In order to solve this problem, the Si or the Si alloy may be mixed with graphite. However, when the graphite may be non-uniformly distributed during the mixing, the cycle characteristics (life) may be deteriorated.

In recent years, with the versatility of lithium ion secondary batteries such as high-output power supplies for plug-in hybrid vehicles, hybrid vehicles, and electric tools and the like, further improvement in rate characteristics is required. Batteries used as the high-output power supplies are required to be charged and discharged at high speed.

In the positive electrode active material currently put to practical use, the theoretical capacity of the positive electrode active material is much lower than that of the negative electrode active material. This makes it necessary to impart high conductivity and ion conductivity to the positive electrode in order to achieve the high capacity and high output of the lithium ion battery. Therefore, in order to improve electron conductivity in the positive electrode, a method for adding a carbon material to an electrode as a conductive auxiliary agent is used. As such a carbon material, graphite, acetylene black, and Ketjen black have been reported. In recent years, examples using carbon nanotube and graphene have been reported. However, if the amount of such a conductive auxiliary agent is increased, the amount of the active material in the electrode decreases, whereby the capacity of the battery decreases.

There has also been proposed an electrode material in which the particle surface of an electrode active material is covered with an organic compound as a carbon source, and the organic compound is then carbonized to form a carbonaceous film on the surface of the electrode active material, whereby carbon of the carbonaceous film is interposed as an electron conductive substance in order to improve the electron conductivity of the electrode material (for example, Patent Document 1). However, the carbonization step requires a long-time heat treatment at a high temperature of 500° C. or higher in an inert gas atmosphere. This heat treatment reduces the capacity of the electrode. Since the electrode material is heated at a high temperature of 500 to 800° C. in a reducing atmosphere or an inert atmosphere during the carbonization treatment, the positive electrode active material itself may also be reduced, whereby the usable positive electrode active material is limited to lithium iron phosphate, lithium nickel phosphate, lithium cobalt phosphate, and lithium manganese phosphate and the like. The carbon source in the case of the other positive electrode active materials is limited to a polymer material having conductivity. As described above, the material suitable for improving the electron conductivity of the electrode material is still limited, and further improvement in the electrode material is desired.

PRIOR ART DOCUMENTS

Patent Documents

Patent Document 1: JP-A 2001-15111

SUMMARY OF INVENTION

Technical Problem

The present invention has been made in view of the above circumstances, and an object of the present invention is to provide an electrode material that can be suitably used as a material for forming an electrode used for a lithium ion secondary battery or the like and can improve the rate characteristics of the battery.

Solution to Problem

As a result of intensive studies to achieve the above object, the present inventors have found that a battery produced using an electrode material containing a small amount of polymer having a fluoflavine skeleton in a side chain and an inorganic active material has excellent rate characteristics, and have completed the present invention.

That is, the present invention provides the following electrode material.

1. An electrode material containing: a polymer having a fluoflavine skeleton in a side chain; and an inorganic active material, wherein the polymer is contained in an amount of 1 wt % or less in a solid content.

2. The electrode material according to 1, wherein the polymer is a polymer containing a repeating unit having the following formula (1):

[Chem. 1]

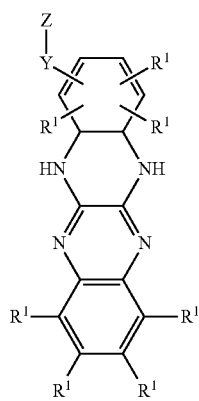

(1)

wherein Z represents a partial structure having the following formula (Z-1), (Z-2), or (Z-3)

[Chem. 2]

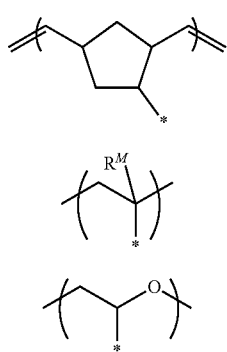

wherein $R^M$ represents a hydrogen atom or a methyl group:
Y represents a single bond, —O—, —CO—, —COO—, —OCO—, —CH$_2$—, —NH—, —NCH$_3$—, —NHCO—, —CONH—, —CH$_2$NHCO—, —CONHCH$_2$—, or —S—:
$R^1$s each independently represent a hydrogen atom, a halogen atom, a hydroxyl group, a carboxy group, an alkyl group having 1 to 10 carbon atoms which may be substituted with a halogen atom, an alkoxy group having 1 to 10 carbon atoms which may be substituted with a halogen atom, or an aryl group having 6 to 12 carbon atoms which may be substituted with a halogen atom; and
* represents a bonding site.

3. The electrode material according to 2, wherein the Z is a partial structure having formula (Z-1).

4. The electrode material according to any one of 1 to 3, wherein all of the $R^1$s are hydrogen atoms.

5. The electrode material according to any one of 1 to 4, wherein the Y is a single bond.

6. The electrode material according to 5, wherein the inorganic active material is at least one selected from a metal, a metalloid, a metal alloy, a metal oxide, a metalloid oxide, a metal phosphate, a metal sulfide, and a metal nitride.

7. The electrode material according to any one of 1 to 6, further containing a solvent.

8. The electrode material according to any one of 1 to 7, further containing a conductive auxiliary agent and a binder.

9. An electrode containing an active material layer made of the electrode material according to any one of 1 to 8.

10. A secondary battery including the electrode according to 9.

11. A polymer containing a repeating unit having the following formula (1):

[Chem. 3]

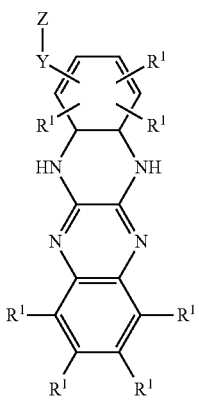

(1)

wherein Z represents a partial structure having the following formula (Z-1), (Z-2), or (Z-3)

[Chem. 4]

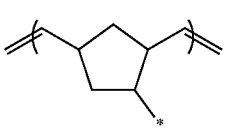

wherein:
$R^M$ represents a hydrogen atom or a methyl group;
Y represents a single bond, —O—, —CO—, —COO—, —OCO—, —CH$_2$—, —NH—, —NCH$_3$—, —NHCO—, —CONH—, —CH$_2$NHCO—, —CONHCH$_2$—, or —S—, provided that when Z is the partial structure having formula (Z-1), Y is not —CH$_2$NHCO—, and when Z is the partial structure having formula (Z-2), Y is not a single bond;

R¹s each independently represent a hydrogen atom, a halogen atom, a hydroxyl group, a carboxy group, an alkyl group having 1 to 10 carbon atoms which may be substituted with a halogen atom, an alkoxy group having 1 to 10 carbon atoms which may be substituted with a halogen atom, or an aryl group having 6 to 12 carbon atoms which may be substituted with a halogen atom; and

* represents a bonding site.

12. The polymer according to 11, wherein the Z is a partial structure having formula (Z-1).

13. The polymer according to 11 or 12, wherein all of the R¹s are hydrogen atoms.

14. The polymer according to any one of 11 to 13, wherein the Y is a single bond.

Advantageous Effects of Invention

By using an electrode material of the present invention, a battery having excellent rate characteristics can be provided.

DESCRIPTION OF EMBODIMENTS

Figure 1:
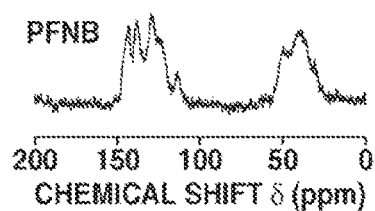
FIG. 1 shows the CP-MS spectrum of a polymer A obtained in Example 1-1.

An electrode material of the present invention contains a polymer having a fluoflavine skeleton in a side chain (hereinafter, may be referred to as a "fluoflavine skeleton-containing polymer" or simply as a "polymer") and an inorganic active material, and the polymer is contained in an amount of 1 wt % or less in a solid content. In the present invention, by using the fluoflavine skeleton-containing polymer in combination with the inorganic active material, a battery excellent in rate characteristics and cycle characteristics can be obtained even when the fluoflavine skeleton-containing polymer is added in a small amount. The solid content referred to herein means components other than a solvent contained in the electrode material of the present invention.

The fluoflavine skeleton-containing polymer is not particularly limited as long as it has a fluoflavine skeleton in a side chain, but in the present invention, a polymer containing a repeating unit represented by the following formula (1) is preferable.

[Chem. 5]

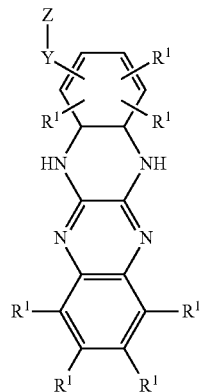

(1)

wherein Z represents a partial structure represented by the following formula (Z-1), (Z-2), or (Z-3)

[Chem. 6]

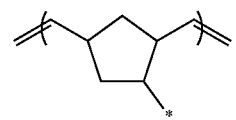

(Z-1)

(Z-2)

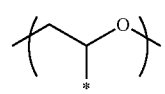

(Z-3)

wherein: * represents a bonding site; and $R^M$ is a hydrogen atom or a methyl group. Among these, a partial structure represented by formula (Z-1) is preferable.

Y represents a single bond, —O—, —CO—, —COO—, —OCO—, —CH₂—, —NH—, —NCH₃—, —NHCO—, —CONH—, —CH₂NHCO—, —CONHCH₂—, or —S—. When Z is a partial structure represented by formula (Z-1) or (Z-3), Y is preferably a single bond. When Z is a partial structure represented by formula (Z-2), Y is preferably —COO—.

R¹s each independently represent a hydrogen atom, a halogen atom, a hydroxyl group, a carboxy group, an alkyl group having 1 to 10 carbon atoms which may be substituted with a halogen atom, an alkoxy group having 1 to 10 carbon atoms which may be substituted with a halogen atom, or an aryl group having 6 to 12 carbon atoms which may be substituted with a halogen atom.

Examples of the halogen atom include a fluorine atom, a chlorine atom, a bromine atom, and an iodine atom.

Examples of the alkyl group having 1 to 10 carbon atoms include a methyl group, an ethyl group, an n-propyl group, an isopropyl group, an n-butyl group, an i-butyl group, an s-butyl group, a t-butyl group, an n-pentyl group, an n-hexyl group, an n-heptyl group, an n-octyl group, an n-nonyl group, and an n-decyl group. Among these, an alkyl group having 1 to 5 carbon atoms is preferable, and an alkyl group having 1 to 3 carbon atoms is more preferable.

Examples of the alkoxy group having 1 to 10 carbon atoms include a methoxy group, an ethoxy group, an n-propoxy group, an i-propoxy group, an n-butoxy group, an i-butoxy group, an s-butoxy group, a t-butoxy group, an n-pentoxy group, an n-hexyloxy group, an n-heptyloxy group, an n-octyloxy group, an n-nonyloxy group, and an n-decyloxy group. Among these, an alkoxy group having 1 to 5 carbon atoms is preferable, and an alkoxy group having 1 to 3 carbon atoms is more preferable.

Examples of the aryl group having 6 to 12 carbon atoms include a phenyl group, a 1-naphthyl group, a 2-naphthyl group, a 1-biphenylyl group, and a 2-biphenylyl group. Among these, a phenyl group is preferable.

In the alkyl group, the alkoxy group, and the aryl group, some or all of hydrogen atoms thereof may be substituted with halogen atoms. Examples of the halogen atom include the same as those exemplified above.

In the present invention. $R^1$ is preferably a hydrogen atom and an alkyl group, and more preferably a hydrogen atom.

$R^M$ represents a hydrogen atom or a methyl group, but a hydrogen atom is preferable.

As an aspect of the repeating unit represented by formula (1), a repeating unit represented by the following formula (1-1) is preferable.

[Chem. 7]

$$\text{(1-1)}$$

In the formula, Z, Y, and $R^1$ are as described above.

More preferred examples of the aspect of the repeating unit represented by formula (1) include, but are not limited to, those represented by the following formulae (2-1) to (2-3).

[Chem. 8]

$$\text{(2-1)}$$

$$\text{(2-2)}$$

$$\text{(2-3)}$$

In the formula, $R^1$ and $R^M$ are as described above.

Preferred specific examples of the repeating unit represented by formula (1) include, but are not limited thereto, those represented by the following formulae (3-1) to (3-3).

[Chem. 9]

(3-1)

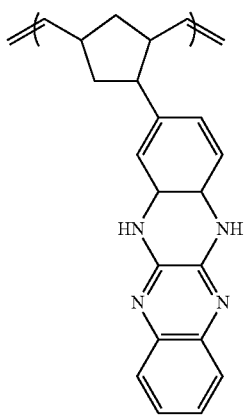

(3-2)

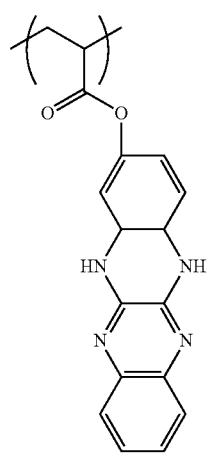

(3-3)

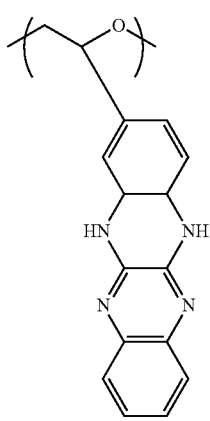

The weight average molecular weight of the fluoflavine skeleton-containing polymer is usually 1,000 to 500,000, and preferably 2,000 to 200,000. The weight average molecular weight is set to be equal to or less than the upper limit of the above range, which makes it easy to dissolve the polymer in a solvent when preparing an electrode slurry (active material layer forming composition) using the polymer. The weight average molecular weight is set to be equal to or greater than to the lower limit of the above range, which makes it possible to prevent the dissolution of the polymer in an electrolytic solution when a battery is produced using an electrode having an active material layer formed using the electrode slurry. In the present invention, the weight average molecular weight is a value in terms of polystyrene measured by gel permeation chromatography (GPC).

The compounding amount of the fluoflavine skeleton-containing polymer is 1 wt % or less in the solid content, and is preferably 0.01 to 0.8 wt %, and more preferably 0.05 to 0.5 wt % from the viewpoint of effectively improving the rate characteristics and cycle characteristics of the obtained secondary battery.

Even when the polymer is added in a small amount as described above in the case where the polymer is used in combination with the inorganic active material, the polymer is considered to exhibit an excellent effect because the polymer itself has charge storage ability. In the present invention, "having charge storage ability" means to provide a discharge capacity of 10 mAh/g or more in a secondary battery including an electrode using only a fluoflavine skeleton-containing polymer having charge storage ability as an active material. The discharge capacity is preferably 30 mAh/g or more, and more preferably 45 mAh/g or more from the viewpoint of improving rate characteristics and cycle characteristics. The upper limit is not particularly limited, but is usually 200 mAh/g or less in consideration of deterioration during cycling. In the present invention, the discharge capacity is within the above range, whereby the decrease in the charge capacity is reduced as compared with the case of compounding a compound having no capacity by itself.

When a polymer containing a repeating unit represented by formula (3-1) is synthesized as the fluoflavine skeleton-containing polymer, for example, a method shown in the following scheme 1 can be mentioned.

Scheme 1

[Chem. 10]

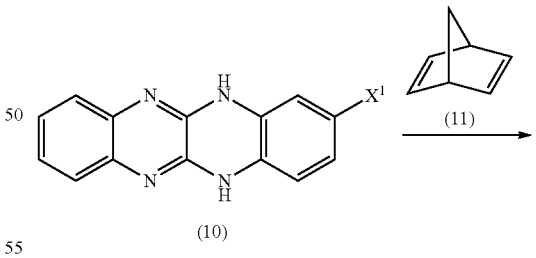

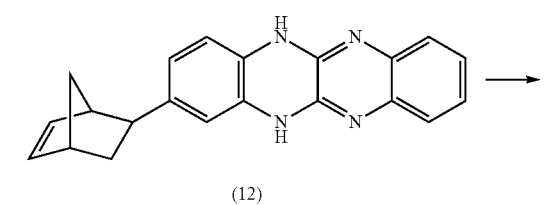

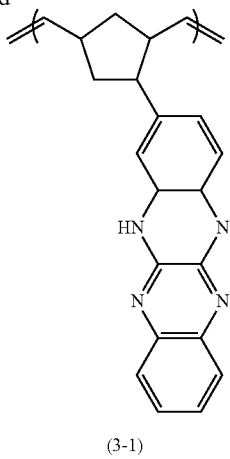

(3-1)

In the formula, X¹ represents a halogen atom.

In the scheme 1, first, a fluoflavine derivative (10) having a halogen atom and 2,5-norbornadiene (11) are reacted in a solvent in the presence of a catalyst to synthesize a fluoflavine skeleton-containing monomer (12) (first stage). The resulting monomer (12) is then polymerized in the presence of a catalyst in a solvent (second stage), whereby a fluoflavine skeleton-containing polymer (3-1) can be synthesized.

The fluoflavine derivative (10) can be synthesized according to a known synthesis method. For example, the fluoflavine derivative (10) can be synthesized with reference to a synthesis method described in Journal of Photochemistry and Photobiology A: Chemistry 198 (2008) 60-68.

Examples of the fluoflavine derivative (10) include, but are not limited to, 2-chloro-5,11-dihydroquinoxalino[2,3-b]quinoxaline and 2-bromo-5,11-dihydroquinoxalino[2,3-b]quinoxaline.

The solvent used in the first stage is not particularly limited as long as it can disperse or dissolve the raw materials to be used. Examples of such a solvent include dimethyl sulfoxide, N,N-dimethylformamide, N,N-dimethylacetamide, N-methyl-2-pyrrolidone, hexamethylphosphoric triamide, acetonitrile, acetone, alcohols (methanol, ethanol, 1-propanol, and 2-propanol and the like), glycols (ethylene glycol and triethylene glycol and the like), cellosolves (ethyl cellosolve and methyl cellosolve and the like), polyhydric alcohols (glycerin and pentaerythritol and the like), tetrahydrofuran, ethyl acetate, butyl acetate, benzene, toluene, xylene, pentane, hexane, heptane, chlorobenzene, dichlorobenzene, trichlorobenzene, hexadecane, benzyl alcohol, and oleylamine and the like. Among these, N,N-dimethylformamide, N,N-dimethylacetamide, and N-methyl-2-pyrrolidone are preferable from the viewpoint of a reaction temperature and a reaction concentration. These solvents may be appropriately selected according to the raw materials to be used. The solvents may be used singly or as a mixture of two or more thereof.

Examples of the catalyst used in the first stage include copper catalysts such as copper chloride, copper bromide, and copper iodide; and palladium catalysts such as Pd(PPh$_3$)$_4$ (tetrakis(triphenylphosphine)palladium), Pd(PPh$_3$)$_2$Cl$_2$(bis(triphenylphosphine)dichloropalladium), Pd(dba)$_2$(bis(dibenzylideneacetone)palladium), Pd$_2$(dba)$_3$ (tris(dibenzylideneacetone)dipalladium), Pd(P-t-Bu$_3$)$_2$(bis(tri(t-butylphosphine)palladium), and Pd(OAc)$_2$(palladium acetate). These catalysts may be used singly or as a mixture of two or more thereof. These catalysts may be used together with known suitable ligands.

Examples of such a ligand include tertiary phosphines such as triphenylphosphine, tri-o-tolylphosphine, diphenylmethylphosphine, phenyldimethylphosphine, trimethylphosphine, triethylphosphine, tributylphosphine, tri-t-butylphosphine, di-t-butyl(phenyl)phosphine, di-t-butyl(4-dimethylaminophenyl)phosphine, 1,2-bis(diphenylphosphino)ethane, 1,3-bis(diphenylphosphino)propane, 1,4-bis(diphenylphosphino)butane, and 1,1'-bis(diphenylphosphino)ferrocene, and tertiary phosphites such as trimethylphosphite, triethylphosphite, and triphenylphosphite.

The amount of the catalyst used may be about 0.01 to 0.2 mol per 1 mol of the fluoflavine derivative represented by formula (10), and is suitably about 0.02 to 0.1 mol.

When a ligand is used, the amount thereof used may be 0.1 to 5 equivalents per a metal complex (catalyst) to be used, and suitably 1 to 2 equivalents.

In the first stage, abase may be used. Examples of the base that can be used include sodium hydride, pyridine, triethylamine, and diisopropylethylamine, and sodium hydride, pyridine, and triethylamine are suitable. The amount of the base to be used is suitably an amount that ranges from 1 mol per 1 mol of the fluoflavine derivative up to a solvent amount.

The compounding ratio (molar ratio) of 2,5-norbornadiene and the fluoflavine derivative is not particularly limited, but from the viewpoint of preventing polymerization between the produced monomers, it is preferable that both the components are equimolar, or 2,5-norbornadiene is excessive per the fluoflavine derivative. In the present invention, the amount of 2,5-norbornadiene used is preferably 1 to 8 mol, and more preferably 1.5 to 5 mol, per 1 mol of the fluoflavine derivative.

A reaction temperature in the first stage may be appropriately set in the range from the melting point to the boiling point of the solvent to be used, and is particularly preferably about 0 to 200° C., and more preferably 30 to 130° C. During heating, reflux may be performed. A reaction time cannot be generally defined because it depends on the reaction temperature and the reactivity of the raw material substance, but is usually about 1 to 48 hours. When the reaction temperature is 30 to 130° C., the reaction time is about 10 to 30 hours. After the completion of the reaction, a post-treatment is performed according to a conventional method, whereby a monomer to be a base of the intended fluoflavine skeleton-containing polymer can be obtained.

In the second stage, the fluoflavine skeleton-containing monomer (12) obtained in the first stage is polymerized in a solvent. The polymerization is usually performed by ring-opening metathesis polymerization. As the conditions, a conventionally known method such as an olefin metathesis reaction using Grubbs' catalyst may be used.

The solvent used in the second stage is not particularly limited as long as it can disperse or dissolve the raw materials to be used. Examples of such a solvent include dimethyl sulfoxide, N,N-dimethylformamide, N,N-dimethylacetamide, N-methyl-2-pyrrolidone, hexamethylphosphoric triamide, acetonitrile, acetone, alcohols (methanol, ethanol, 1-propanol, and 2-propanol and the like), glycols (ethylene glycol and triethylene glycol and the like), cellosolves (ethyl cellosolve and methyl cellosolve and the like), polyhydric alcohols (glycerin and pentaerythritol and the like), tetrahydrofuran, ethyl acetate, butyl acetate, benzene, toluene, xylene, pentane, hexane, heptane, chlorobenzene, dichlorobenzene, trichlorobenzene, hexadecane, benzyl alcohol, and oleylamine. Among these, N,N-dimethylformamide, N,N-dimethylacetamide, and N-methyl-2-pyrrolidone are preferable from the viewpoint of a reaction temperature and a reaction concentration. These solvents may be appropriately selected according to the raw materials to be used. The solvents may be used singly or as a mixture of two or more thereof.

When the polymerization is performed by the ring-opening metathesis reaction, various Grubbs' catalysts can be used as the catalyst, but third generation Grubbs' catalyst can be suitably used in the present invention. The amount of the catalyst used may be about 0.005 to 0.1 mol per 1 mol of the monomer, and is suitably about 0.005 to 0.05 mol.

The reaction temperature may be appropriately set in the range from the melting point to the boiling point of the solvent to be used, and is particularly preferably about 0 to 200° C., and more preferably 20 to 100° C. During heating, reflux may be performed. A reaction time cannot be generally defined because it depends on the reaction temperature and the reactivity of the raw material substance, but is usually about 1 to 48 hours. When the reaction temperature is 20 to 100° C., the reaction time is about 1 to 10 hours. After the completion of the reaction, a post-treatment is performed according to a conventional method, whereby the intended fluoflavine skeleton-containing polymer can be obtained.

When a polymer containing a repeating unit represented by formula (3-2) is synthesized as the fluoflavine skeleton-containing polymer, for example, a method shown in the following scheme 2 can be mentioned.

Scheme 2

[Chem. 11]

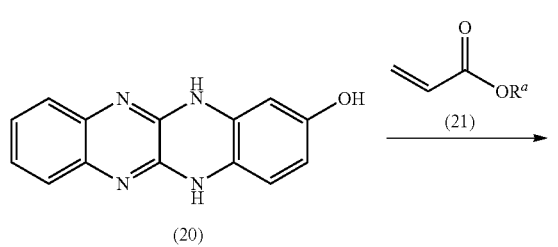

(20)

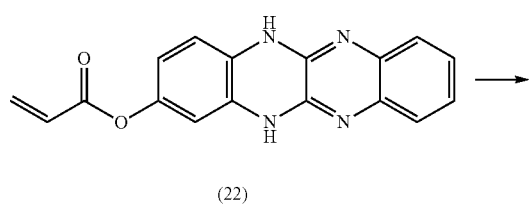

(22)

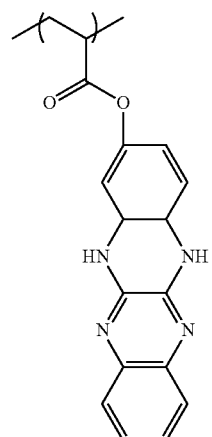

(3-2)

In the formula, $R^a$ represents a methyl group, an ethyl group, a propyl group, or a butyl group.

In scheme 2, first, a fluoflavine skeleton-containing polymer monomer (22) is synthesized by a transesterification reaction of 2-hydroxy-5,11-dihydroquinoxalino[2,3-b]quinoxaline (20) and an acrylic acid ester compound (21) (first stage). The resulting monomer (22) is then polymerized in the presence of a catalyst in a solution (second stage), whereby a fluoflavine skeleton-containing polymer (3-2) can be synthesized.

The fluoflavine derivative (20) can be synthesized according to a known synthesis method. For example, the fluoflavine derivative (10) can be synthesized with reference to a synthesis method described in Journal of Photochemistry and Photobiology A: Chemistry 198 (2008) 60-68.

Examples of the acrylic acid ester compound (21) include methyl acrylate, ethyl acrylate, propyl acrylate, and butyl acrylate.

The solvent used in the transesterification reaction is not particularly limited as long as it can disperse or dissolve the raw materials to be used. Examples of such a solvent include dimethyl sulfoxide, N,N-dimethylformamide, N,N-dimethylacetamide, N-methyl-2-pyrrolidone, hexamethylphosphoric triamide, acetonitrile, acetone, alcohols (methanol, ethanol, 1-propanol, and 2-propanol and the like), glycols (ethylene glycol and triethylene glycol and the like), cellosolves (ethyl cellosolve and methyl cellosolve and the like), polyhydric alcohols (glycerin and pentaerythritol and the like), tetrahydrofuran, benzene, toluene, xylene, pentane, hexane, heptane, chlorobenzene, dichlorobenzene, trichlorobenzene, hexadecane, benzyl alcohol, and oleylamine. These solvents may be appropriately selected according to the raw materials to be used. The solvents may be used singly or as a mixture of two or more thereof.

In the transesterification reaction, an appropriate acid or base can be used as a catalyst. Specific examples thereof include inorganic acids such as hydrochloric acid, sulfuric acid, nitric acid, and phosphoric acid; organic carboxylic acids such as acetic acid, propionic acid, phthalic acid, and benzoic acid; organic sulfonic acids such as methylsulfonic acid, benzenesulfonic acid, p-toluenesulfonic acid, and trifluoromethanesulfonic acid; alkali metal or alkaline earth metal hydroxides such as sodium hydroxide, potassium hydroxide, and magnesium hydroxide; and carbonates and hydrogen carbonates of alkali metals or alkaline earth metals such as sodium hydrogen carbonate, potassium carbonate, and calcium hydrogen carbonate.

In the transesterification reaction, a known polymerization inhibitor may be added. Examples of the polymerization inhibitor include phenols such as hydroquinone and hydroquinone monomethyl ether; sulfur compounds such as phenothiazine and ethylene thiourea; copper salts such as copper dibutyldithiocarbamate; manganese salts such as manganese acetate; a nitro compound, a nitroso compound, and an N-oxyl compound such as 4-hydroxy-2,2,6,6-tetramethylpiperidinoxyl.

The transesterification reaction can be performed by a method generally known to those skilled in the art as a method for producing an acrylic acid ester. During the transesterification reaction, it is necessary to azeotropically distill off a lower alcohol produced as a by-product with a lower acrylic acid ester and/or a solvent. Therefore, as the reaction apparatus, for example, a batch type reaction tank including a rectifying tower is used.

In the second stage, the fluoflavine skeleton-containing monomer (22) obtained in the first stage is polymerized in a solvent. The polymerization method is not particularly limited, and can be appropriately selected from polymerization methods usually used in polymerization of an acrylic polymer. Examples of the polymerization method include a solution polymerization method, an emulsion polymerization method, and a suspension polymerization method.

When a polymer containing a repeating unit represented by formula (3-3) is synthesized as the fluoflavine skeleton-containing polymer, for example, a method shown in the following scheme 3 can be mentioned.

Scheme 3

[Chem. 12]

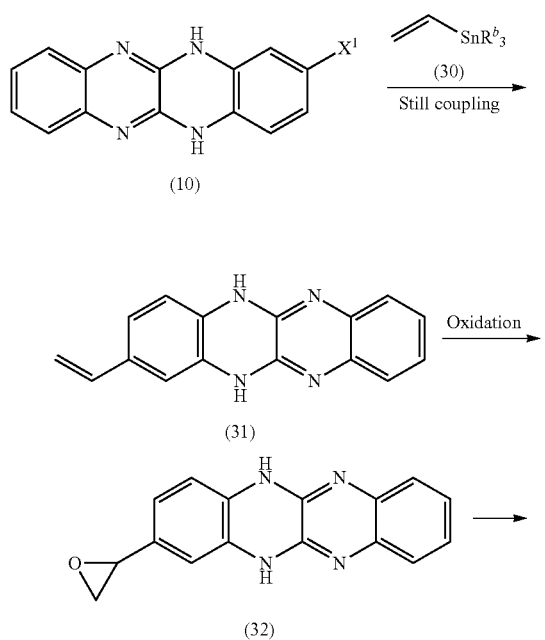

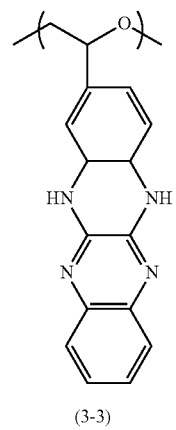

(3-3)

In the formula, $R^b$ represents a methyl group, an ethyl group, an n-propyl group, or an n-butyl group, and $X^1$ is as described above.

In scheme 3, first, a vinyl group is introduced into a fluoflavine derivative (10) by a stille-cross coupling reaction using an organotin compound (30) in the presence of a palladium catalyst in a solvent to synthesize a fluoflavine derivative (31) (first stage), and a C=C double bond of the introduced vinyl group is then oxidized and epoxidized to obtain a fluoflavine skeleton-containing monomer (32) (second stage). The resulting monomer (32) is then polymerized (third stage), whereby a fluoflavine skeleton-containing polymer (3-3) can be synthesized.

In the first stage, as the palladium catalyst, those known for being used for the stille-cross coupling reaction can be used, and for example, those similar to the palladium catalyst exemplified in the reaction between (10) and (11) above can be mentioned.

The organotin compound (30) is preferably one in which $R^b$ is an n-butyl group from the viewpoint of increasing a reaction rate and suppressing a side reaction.

The solvent used in the stille-cross coupling is not particularly limited as long as it can disperse or dissolve raw materials to be used. Examples of such a solvent include dimethyl sulfoxide, N,N-dimethylformamide, N,N-dimethylacetamide, N-methyl-2-pyrrolidone, hexamethylphosphoric triamide, acetonitrile, acetone, alcohols (methanol, ethanol, 1-propanol, and 2-propanol and the like), glycols (ethylene glycol and triethylene glycol and the like), cellosolves (ethyl cellosolve and methyl cellosolve and the like), polyhydric alcohols (glycerin and pentaerythritol and the like), tetrahydrofuran, ethyl acetate, butyl acetate, benzene, toluene, xylene, pentane, hexane, heptane, chlorobenzene, dichlorobenzene, trichlorobenzene, hexadecane, benzyl alcohol, and oleylamine and the like. These solvents may be appropriately selected according to the raw materials to be used. The solvents may be used singly or as a mixture of two or more thereof.

The allyl group introduced in the second stage can be oxidized by a known method such as a method of oxidizing an allyl group with an oxidizing agent such as peroxide.

In the third stage, the fluoflavine skeleton-containing monomer (32) obtained in the second stage is polymerized. In the polymerization, the method and the conditions may be appropriately selected from methods and conditions usually used in the cationic ring-opening polymerization of epoxides.

As the inorganic active material (hereinafter, may be simply referred to as an "active material"), various active materials conventionally used for an electrode for an energy storage device such as a secondary battery can be used, and examples thereof include a metal, a metalloid, a metal alloy, a metal oxide, a metalloid oxide, a metal phosphate, a metal sulfide, and a metal nitride.

Specific examples of the inorganic active material include the following materials.

Examples of the metal active material include Al, Sn, and Zn.

Examples of the semimetal active material include Si, Ge, and As.

Examples of the metal alloy active material include Li—Al-based alloys, Li—Mg-based alloys, Li—Al—Ni-based alloys, Na—Hg-based alloys, and Na—Zn-based alloys.

Examples of the metal oxide active material include $AlO_x$, $SnO_x$, $SbO_x$, $BiO_x$, $PbO_x$, $ZnO_x$, $CdO_x$, $InO_x$, $TiO_x$, and $GaO_x$, provided that $0<x\leq2$, $V_2O_6$, $V_6O_{13}$, $MnO_2$, $LiCoO_2$, $LiMnO_2$, $LiMn_2O_4$, $LiMo_2O_4$, $LiV_3O_8$, $LiNiO_2$, $Li_zNi_yM_{1-y}O_2$, provided that M represents at least one metal element selected from Co, Mn, Ti, Cr, V, Al, Sn, Pb, and Zn, $0.05\leq z\leq1.10$, $0.5\leq y\leq1.0$, ternary active materials ($Li(Ni_aCo_bMn_c)O_2$, provided that $0<a<1$, $0<b<1$, $0<c<1$, $a+b+c=1$), tin silicon oxides ($SnSiO_3$), lithium bismuth oxides ($Li_3BiO_4$), lithium zinc oxides ($Li_2ZnO_2$), and lithium titanium oxides ($Li_4Ti_5O_{12}$).

Examples of the metalloid oxide active material include $SiO_x$, $GeO_x$, and $AsO_x$, provided that $0<s\leq2$.

Examples of the metal phosphate active material include lithium iron phosphate ($LiFePO_4$, LFP).

Examples of the metal sulfide active material include $FeS_2$, $TiS_2$, $MoS_2$, $Li_2S$, lithium iron sulfide ($Li_xFeS_2$, provided that $0<x\leq3$), and lithium copper sulfide ($Li_xCuS$, provided that $0<x\leq3$).

Examples of the metal nitride active material include $Li_xM_yN$, provided that M=Co, Ni, Cu, $0\leq x\leq3$, $0\leq y\leq0.5$, x and y do not become 0 at the same time, and lithium iron nitride ($Li_3FeN_4$).

In the present invention, among these, $FeS_2$, $TiS_2$, $MoS_2$, $LiFePO_4$, $V_2O_6$, $V_6O_{13}$, $MnO_2$, $LiCoO_2$, $LiMnO_2$, $LiMn_2O_4$, $LiMo_2O_4$, $LiV_3O_8$, $LiNiO_2$, $Li_zNi_yM_{1-y}O_2$, provided that M represents at least one metal element selected from Co, Mn, Ti, Cr, V, Al, Sn, Pb, and Zn, $0.05\leq s\leq1.10$, $0.5\leq y\leq1.0$, $Li(Ni_aCo_bMn_c)O_2$, provided that $0<a<1$, $0<b<1$, $0<c<1$, $a+b+c=1$, $Li_4Ti_5O_{12}$, Si, $SiO_x$, $AlO_x$, $SnO_x$, $SbO_x$, $BiO_x$, $GeO_x$, $AsO_x$, $PbO_x$, $ZnO_x$, $CdO_x$, $InO_x$, $TiO_x$, and $GaO_x$, provided that $0<x\leq2$, are preferable, and $LiFePO_4$ is more preferable.

Furthermore, $Li(Ni_aCo_bMn_c)O_2$ more preferably satisfies $1/3\leq a<1$, $0<b\leq1/3$, $0<c\leq1/3$, and $a+b+c=1$.

The $Li(Ni_aCo_bMn_c)O_2$ can also be obtained as a commercially available product, and examples of such a commercially available product include NCM111 (manufactured by Beijing Easping Material Technology, manufactured by Toshima Manufacturing Co., Ltd., $a=1/3$, $b=1/3$, $c=1/3$), NCM523 (manufactured by Beijing Easping Material Technology, manufactured by JIANGSU Easping Material Technology, $a=0.5$, $b=0.2$, $c=0.3$), NCM622 (manufactured by Beijing Easping Material Technology, $a=0.6$, $b=0.2$, $c=0.2$), and NCM811 (manufactured by Beijing Easping Material Technology, $a=0.8$, $b=0.1$, $c=0.1$).

The compounding amount of the inorganic active material varies depending on required electrical and thermal characteristics, viscosity of the composition, and production cost, and the like, but is preferably 80 to 99.8 wt %, more preferably 85 to 98.5 wt %, and still more preferably 89 to 98 wt % in the solid content.

The mass ratio of the inorganic active material and the fluoflavine skeleton-containing polymer (inorganic active material:fluoflavine skeleton-containing polymer) is preferably 100:0.01 to 100:1.25, more preferably 100:0.1 to 100:1.05, still more preferably 100:0.1 to 100:0.9, and still more preferably 100:0.1 to 100:0.6. By setting the mass ratio within the above range, the rate characteristics and cycle characteristics of the obtained secondary battery can be effectively improved.

The electrode material of the present invention preferably further contains a conductive auxiliary agent, a binder, and a solvent (dispersion medium) as necessary.

Examples of the conductive auxiliary agent include carbon materials such as graphite, carbon black, acetylene black, vapor-grown carbon fibers, carbon nanotubes, carbon nanohorns and graphene, and conductive polymers such as polyaniline, polypyrrole, polythiophene, polyacetylene and polyacene. The conductive auxiliary agents can be used singly or as a mixture of two or more thereof.

The compounding amount of the conductive auxiliary agent is not particularly limited, but is preferably 0.05 to 9 wt %, more preferably 0.1 to 6 wt %, and still more preferably 0.2 to 3 wt % in the solid content. By setting the compounding amount of the conductive auxiliary agent within the above range, good electrical conductivity can be obtained.

The binder to be used can be appropriately selected from known materials, and is not particularly limited. Examples of the binder which can be used in the present invention include polyvinylidene fluoride (PVdF), polytetrafluoroethylene, a tetrafluoroethylene-hexafluoropropylene copolymer, a vinylidene fluoride-hexafluoropropylene copolymer, a vinylidene fluoride-chlorotrifluoroethylene copolymer, polyvinyl alcohol, polyimide, an ethylene-propylene-diene ternary copolymer, styrene-butadiene rubber, carboxymethyl cellulose, polyacrylic acid, polyaniline, polyvinyl pyrrolidone, tetrafluoroethylene, polyethylene, and polypropylene. These can be used singly or in combination of two or more thereof.

The compounding amount of the binder is not particularly limited, but is preferably 0.1 to 15 wt %, more preferably 0.5 to 12 wt %, and still more preferably 1 to 10 wt % in the solid content. By setting the compounding amount of the binder within the above range, good adhesiveness to a current collecting substrate can be obtained without the capacity being lowered.

The binder to be used may be dissolved in an appropriate solvent to be described later in advance before mixing, as necessary.

The solvent is not particularly limited as long as it can disperse or dissolve raw materials to be used. Examples of such a solvent include water, dimethylsulfoxide. N,N-dimethylformamide, N,N-dimethylacetamide, N-methyl-2-pyrrolidone (NMP), hexamethylphosphoric triamide, acetonitrile, acetone, alcohols (methanol, ethanol, 1-propanol, and 2-propanol and the like), glycols (ethylene glycol and triethylene glycol and the like), cellosolves (ethyl cellosolve and methyl cellosolve and the like), polyhydric alcohols (glycerin and pentaerythritol and the like), tetrahydrofuran, ethyl acetate, butyl acetate, benzene, toluene, xylene, pentane, hexane, heptane, chlorobenzene, dichlorobenzene, trichlorobenzene, hexadecane, benzyl alcohol, and oleylamine. Among these, water, NMP, dimethyl sulfoxide, ethylene carbonate, propylene carbonate, dimethyl carbonate, diethyl carbonate, methylethyl carbonate, γ-butyrolactone, tetrahydrofuran, dioxolane, sulfolane, dimethylformamide, and dimethylacetamide and the like are preferable. These solvents may be appropriately selected according to the raw materials to be used, but NMP is suitable when a water-insoluble binder such as PVdF is used. The solvents may be used singly or as a mixture of two or more thereof.

When an electrode material for forming an active material layer is prepared, a preparation method thereof is not particularly limited, and the electrode material may be prepared by compounding components in any order.

In the fluoflavine skeleton-containing polymer, when the solvent used in the synthesis is the same as or a solvent miscible with the solvent exemplified above, the obtained reaction liquid may be used as it is. Meanwhile, when the solvent used for the synthesis of the fluoflavine skeleton-containing polymer is a solvent which is not miscible with the solvent exemplified above, it is preferable to use a liquid isolated by removing the solvent from the obtained reaction liquid or a liquid substituted with an appropriate solvent.

The electrode of the present invention is obtained by forming an active material layer (thin film) made of the electrode material described above on a substrate which is a current collector.

When the active material layer is formed on a substrate, examples of a method for forming the active material layer include a method in which an electrode-forming composition prepared without using a solvent is pressure-molded on a substrate (dry method), or a method in which an electrode-forming composition (electrode slurry) is prepared using a solvent, applied to a current collector, and dried (wet method). These methods are not particularly limited, and various conventionally known methods can be used. Examples of the wet method include various printing methods such as offset printing and screen printing, a doctor blade method, a dip coating method, a spin coating method, a bar coating method, a slit coating method, and an inkjet method.

Examples of the substrate used for the electrode include metal substrates composed of platinum, gold, iron, stainless steel, copper, aluminum, and lithium and the like, alloy substrates composed of any combination of these metals, oxide substrates composed of Indium-tin oxide (ITO), indium-zinc oxide (IZO), and antimony-tin oxide (ATO) and the like, or carbon substrates composed of glassy carbon, pyrolytic graphite, and carbon felt and the like.

The film thickness of the active material layer is not particularly limited, but is preferably about 0.01 to 1,000 μm, and more preferably about 1 to 200 μm. When the thin film is used alone as the electrode, the film thickness thereof is preferably 10 μm or more.

In order to further suppress the elution of the active material contained in the electrode, the active material layer may further contain a polyalkylene oxide and an ion conductive salt, or the electrode may be covered with a protective film. The protective film preferably contains a polyalkylene oxide and an ion conductive salt.

The polyalkylene oxide is not particularly limited, but polyethylene oxide and polypropylene oxide and the like are preferable.

The numerical average molecular weight of the polyalkylene oxide is preferably 300,000 to 900,000, and more preferably 500,000 to 700,000. The numerical average molecular weight is a value measured in terms of polystyrene by gel permeation chromatography (GPC) using tetrahydrofuran as a solvent.

Examples of the ion conductive salt include lithium bis(trifluoromethanesulfonyl)imide (LiTFSI), lithium bis(pentafluoroethanesulfonyl)imide (LiBETI), lithium trifluoromethanesulfonate (LiCF$_3$SO$_3$), lithium perchlorate (LiClO$_4$), lithium tetrafluoroborate (LiBF$_4$), and lithium hexafluorophosphate (LiPF$_6$). The ion conductive salt is preferably contained in an amount of 5 to 50 parts by weight per 100 parts by weight of the polyalkylene oxide.

The protective film can be formed, for example, by applying a composition containing a polyalkylene oxide, an ion conductive salt, and a solvent on a substrate on which the active material layer is formed by a method such as a dip method, and drying the composition at 40 to 60° C. for 30 to 120 minutes.

As the solvent, acetonitrile and dichloromethane and the like are preferable.

The film thickness of the protective film is not particularly limited, but is preferably about 10 to 1,000 μm, and more preferably about 50 to 500 μm.

The secondary battery of the present invention includes the above-described electrodes. More specifically, the secondary battery includes at least a pair of positive and negative electrodes, a separator interposed between the respective electrodes, and an electrolyte. At least one of the positive and negative electrodes includes the above-described electrodes. Other constituent members of the battery element to be used may be appropriately selected from conventionally known constituent members.

Examples of the material used for the separator include porous polyolefins, polyamides, and polyesters.

As the electrolyte, an electrolytic solution composed of an electrolyte salt, which is a main body of ion conduction, and a solvent and the like can be suitably used from the viewpoint of being capable of easily exhibiting a practically sufficient performance.

Examples of the electrolyte salt include lithium salts such as LiPF$_6$, LiBF$_4$, LiN(C$_2$F$_5$SO$_2$)$_2$, LiAsF$_6$, LiSbF$_6$, LiAlF$_4$, LiGaF$_4$, LiInF$_4$, LiClO$_4$, LiN(CF$_3$SO$_2$)$_2$, LiCF$_3$SO$_3$, LiSiF$_6$, and LiN (CF$_3$SO$_2$) (C$_4$F$_9$SO$_2$), metal iodides such as LiI, NaI, KI, CsI, and CaI$_2$, iodide salts of quaternary imidazolium compounds, iodide salts and perchlorate salts of tetraalkylammonium compounds, and metal bromides such as LiBr, NaBr, KBr, CsBr, and CaBr$_2$. These electrolyte salts can be used singly or as a mixture of two or more thereof.

The solvent is not particularly limited as long as it does not cause corrosion or decomposition of the substance constituting the battery to deteriorate the performance, and dissolves the electrolyte salt. For example, cyclic esters such as ethylene carbonate, propylene carbonate, butylene carbonate, and γ-butyrolactone, ethers such as tetrahydrofuran and dimethoxyethane, and chain esters such as dimethyl carbonate, diethyl carbonate, and ethyl methyl carbonate, and the like are used as the nonaqueous solvent. These solvents can be used singly or as a mixture of two or more thereof.

The electrode may be pressed as necessary. At this time, the pressing pressure is preferably 1 kN/cm or more. As the pressing method, a generally employed method can be used, but a die pressing method or a roll pressing method is particularly preferable. The pressing pressure is not particularly limited, but is preferably 2 kN/cm or more, and more preferably 3 kN/cm or more. The upper limit of the pressing pressure is preferably about 40 kN/cm, and more preferably about 30 kN/cm.

The battery produced using the electrode material has more excellent rate characteristics and cycle characteristics than those of a general secondary battery.

The form of the secondary battery and the type of the electrolyte are not particularly limited. Any form of a lithium ion battery, a nickel hydrogen battery, a manganese battery, and an air battery and the like may be used, but a lithium ion battery is suitable. The lamination method and the production method are also not particularly limited.

The form of the cell is not also particularly limited, and cells of various known forms such as a cylindrical cell, a flat wound prismatic cell, a stacked prismatic cell, a coin cell, a flat wound laminate cell, and a stacked laminate cell may be adopted.

In the case of application to the coin cell, the above-mentioned electrode of the present invention to be used may be punched into a predetermined disk shape.

For example, a lithium ion secondary battery can be prepared by installing one electrode on a coin cell cap to which a washer and a spacer had been welded, stacking a separator impregnated with an electrolytic solution and having the same shape thereon, further stacking the electrode of the present invention from above with an active material layer facing down, and placing a case and a gasket, followed by sealing with a coin cell crimper.

EXAMPLES

Hereinafter, the present invention is described in more detail with reference to Examples and Comparative Examples, but the present invention is not limited to the following Examples. Apparatus and measurement conditions used are as follows.

(1) Planetary Centrifugal Mixer

Awatori Rentaro AR-100 manufactured by Thinky (2) Ball Mill Kneading

Mini-Mill pulverisette 23 manufactured by FRISCH (3) $^1$H-NMR Spectrum

ECX-500 Nuclear Magnetic Resonance Spectrometer manufactured by JEOL Ltd. (solvent: dimethylsulfoxide-$d_6$ (DMSO-$d_6$), internal standard: tetramethylsilane)

(4) IR Spectrum

FT/IR-6100 Fourier-Transform Infrared Spectrometer manufactured by JASCO Corporation (5) Elemental Analysis PE2400 Series II Elemental Analyzer manufactured by Perkin Elmer (6) Measurement of Molecular Weight RID-10A/CBM-20A/DGU-20A3/LC-20AD/SPD-20A/CTO-20A manufactured by Shimadzu Corporation (Column: TSgel SuperAW-H manufactured by Shimadzu Corporation, column temperature: 50° C., solvent: DMF, detector: UV (275 nm)-RI detector (internal), calibration curve: standard polystyrene)

(7) CV Measurement, Characterization of Battery

ALSCH 1760EW manufactured by BAS Inc.

(8) CP-MS Spectra

ECA-400 Nuclear Magnetic Resonance Spectrometer manufactured by JEOL Ltd.

[1] Synthesis of Polymer A

[Example of Synthesis 1] Synthesis of 2-bromo-5,11-dihydroquinoxalino[2,3-b]quinoxaline (BrFF)

[Chem. 13]

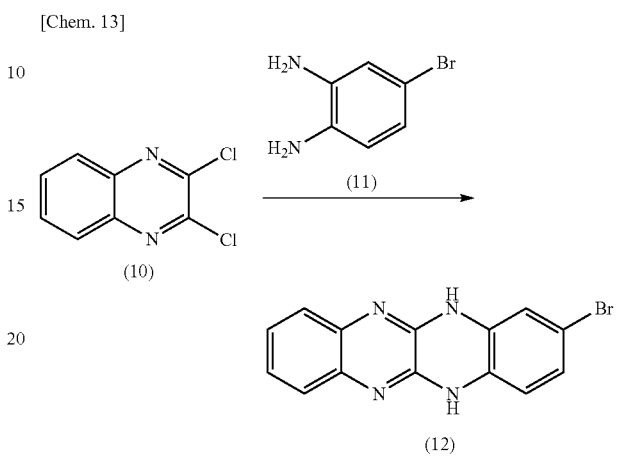

2-bromo-5,11-dihydroquinoxalino[2,3 b]quinoxaline (12) was synthesized as follows with reference to a method described in Journal of Photochemistry and Photobiology A: Chemistry 198 (2008) 60-68.

1.0 g (5.35 mmol) of 4-bromo-1,2-phenylenediamine (11) (manufactured by Tokyo Chemical Industry Co., Ltd.) and 1.6 g (12) (8.03 mmol) of 2,3-dichloroquinoxaline (manufactured by Aldrich) were added into a 100-mL flask, and 10 mL of ethylene glycol was added thereto. Then, the mixture was reacted at 150° C. for 2 hours. After the completion of the reaction, precipitation purification in methanol and recrystallization with acetic acid were performed, followed by vacuum drying to obtain 2-bromo-5,11-dihydroquinoxalino[2,3-b]quinoxaline (12) as brown crystals.

[Example of Synthesis 2] Synthesis of 2-norbornene-5,11-dihydroquinoxalino[2,3-b]quinoxaline (FFNB)

[Chem. 14]

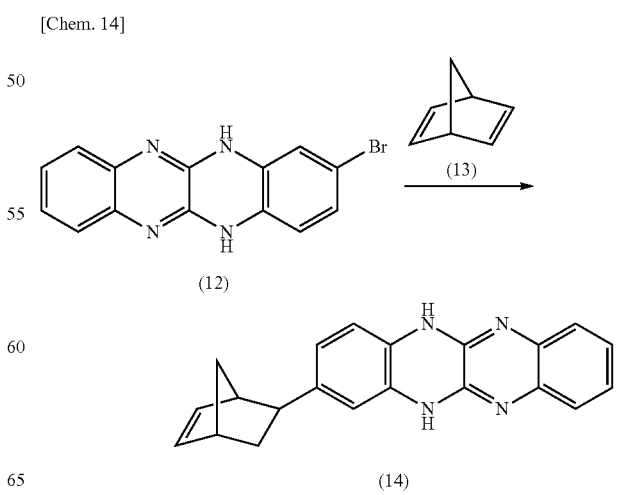

Into a 100-mL flask were added 200 mg (0.641 mmol) of 2-bromo-5,11-dihydroquinoxalino[2,3-b]quinoxaline (12) obtained in Example of Synthesis 1, 11 mg (0.0160 mmol) of bis(triphenylphosphine)palladium (II) dichloride (manufactured by Tokyo Chemical Industry Co., Ltd.), 200 μL (1.92 mmol) of 2,5-norbornadiene (13) (manufactured by Tokyo Chemical Industry Co., Ltd.), 190 μL (1.92 mmol) of triethylamine (manufactured by KANTO KAGAKU), 60 μL (1.28 mmol) of formic acid (manufactured by KANTO KAGAKU), and 40 mL of N,N-dimethylformamide (DMF), and the mixture was reacted at 80° C. for 24 hours in a nitrogen atmosphere. After the completion of the reaction, column purification was performed with a mixed solvent of ethyl acetate/hexane (=4/6 (V/V)), and recrystallization was performed with a mixed solvent of methanol/acetic acid (=3/1 (V/V)), followed by vacuum drying to obtain 2-norbornene-5,11-dihydroquinoxalino[2,3-b]quinoxaline (14) as yellow crystals.

[Example 1-1] Synthesis of Polymer A (PFNB)

Into a 30-mL flask were added 2-norbornene-5,11-dihydroquinoxalino[2,3-b] quinoxaline (14) (500.0 mg, 1.54 mmol) obtained in Example of Synthesis 2, Grubbs' catalyst: 3rd generation (manufactured by Aldrich) (13.6 mg, 0.0154 mmol) and 31 mL of DMF, and the mixture was reacted at 60° C. for 3 hours. The reaction solution was added dropwise to 300 mL of methanol, and the precipitated solid was filtered off. An insoluble matter was collected through Soxhlet purification with methanol, followed by vacuum drying to obtain a polymer A composed of a repeating unit represented by the following formula (3-1) as a brown solid. The polymer A had a numerical average molecular weight Mn of $3.0 \times 10^4$, a weight average molecular weight Mw of $4.2 \times 10^4$, and a dispersion Mw/Mn of 1.40 (Mn is a numerical average molecular weight measured under the same conditions as those of Mw. The same applies hereinafter.). CP-MS spectra are shown in FIG. 1.

[Chem. 15]

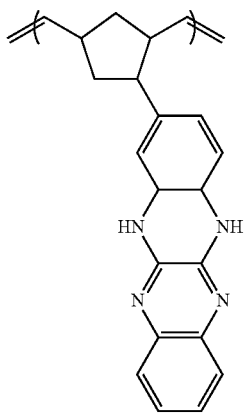

(3-1)

[Comparative Example 1-1] Synthesis of Polyvinyl Anthraquinone (PVAQ)

Into a 10-mL ampoule tube were added 100 mg of 2-vinylanthraquinone (manufactured by Tokyo Chemical Industry Co., Ltd.) and 0.709 mg of AIBN (manufactured by Tokyo Chemical Industry Co., Ltd.), and 2.14 mL of 1,2-dichloroethane was added thereto. The mixture was then reacted at 60° C. for 14 hours. The reaction solution was added dropwise to 100 mL of methanol, and the precipitated solid was filtered off. An insoluble matter was collected through Soxhlet purification with methanol, followed by vacuum drying to obtain PVAQ as a yellow solid. PVAQ had a numerical average molecular weight Mn of $3.3 \times 10^4$, a weight average molecular weight Mw of $7.2 \times 10^4$, and a dispersion Mw/Mn of 2.2.

[2] Evaluation of Electrode and Battery Containing Polymer

[Example 2] CV Measurement of Thin Film Electrode Produced Using Polymer A

Into a ball mill, 5 mg of a polymer A, 40 mg of a vapor-grown carbon fiber, and 250 mg of an NMP solution containing 2 wt % of PVDF were added, and kneaded for 15 minutes to obtain an electrode slurry. The obtained electrode slurry was applied onto an aluminum foil, and heated and vacuum-dried at 80° C. for 16 hours to obtain a thin film electrode (film thickness: about 20 μm).

The obtained electrode was used as a positive electrode, and metal lithium was used as a negative electrode. An EC/DEC (=3/7(v/v)) solution of 1 mol/L lithium hexafluorophosphate was selected as an electrolytic solution to prepare a polymer lithium secondary battery. The polymer lithium secondary battery was prepared by the following method. A polymer/carbon composite electrode was cut to have a radius of 10 mm, and a separator was cut to have a radius of 16 mm. A plastic gasket, a carbon composite electrode, a separator, metal lithium, a spacer, and a washer were laminated in this order on a positive terminal case. A cap was fitted, and sufficiently caulked using a caulking machine holder to prepare a polymer lithium secondary battery (coin cell).

Figure 2:
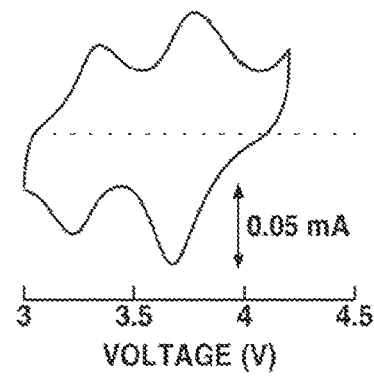
FIG. 2 shows the cyclic voltammogram of a polymer lithium secondary battery prepared in Example 2.

CV measurement was performed at a scan rate of 5 m V/sec using this coin cell. The results are shown in FIG. 2. From the results in FIG. 2, it was confirmed that in the thin film electrode prepared using the polymer A, an oxidation-reduction wave appears at $E_{1/2}$=3.3 V and 3.7 V, and is stable even after repeated sweeping.

Figure 3:
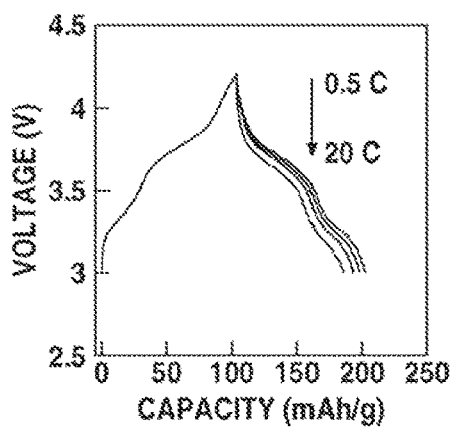
FIG. 3 is a graph showing the measurement result of a potential difference from a reference electrode when a charge/discharge capacity in a polymer lithium secondary battery prepared in Example 2 is changed.
Figure 4:
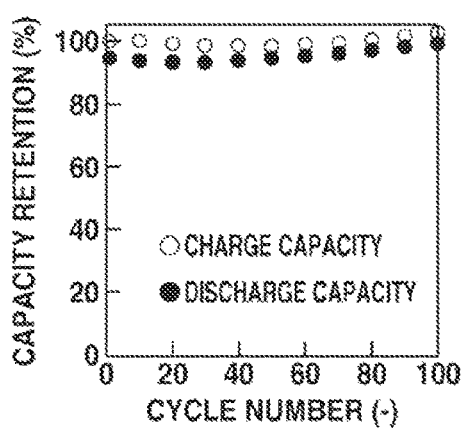
FIG. 4 is a diagram showing the charge/discharge cycle characteristics of the polymer lithium secondary battery prepared in Example 2.

A battery prepared in the same manner was charged at a constant current of 5.78 μA (0.5 C) until the voltage reached 4.2 V, and then discharged at 5.78 μA (0.5 C). As a result, the voltage became almost constant around 3.3 and 3.6 V, and then rapidly decreased. The discharge capacity became 99 mAh/g (theoretical capacity ratio: 60%). The coulombic efficiency was about 91%. This confirmed that the polymer A operates as an effective charge storage material. When the voltage increased to 4.2 V, charge was performed again, and charge and discharge were further repeated 50 times in the range of 3.0 to 4.2 V. FIG. 3 shows the measurement results of a potential difference from a reference electrode when a charge-discharge capacity is changed, and FIG. 4 shows cycle characteristics at the time of charge and discharge. The charge-discharge capacity was maintained at 98% or more even after the charge and discharge were repeated 100 times.

[3] Hybrid Electrode Containing Fluoflavine Skeleton-Containing Polymer and

Inorganic Active Material, and Production of Lithium Ion Battery Using Electrode Example 3-1

0.475 g of lithium iron phosphate (LFP, TATUNG FINE CHEMICALS CO.) as an inorganic active material, 0.0525 g of an N-methylpyrrolidone (NMP) solution containing 1 wt % of the polymer A produced in Example 1-1, 0.352 g of an NMP solution of polyvinylidene fluoride (PVdF) (12 wt %, Kureha Corporation, KF Polymer L #1120) as a binder, 0.0106 g of acetylene black (solid content mass ratio: 89.9:0.1:8.0:2.0) as a conductive auxiliary agent, and 0.210 g of NMP were mixed such that a total solid content concentration was 48 wt %. This was mixed with a planetary centrifugal mixer (3 times at 2,000 rpm for 10 minutes) to prepare an electrode-forming slurry. This was uniformly spread on an aluminum foil (EQ-CC-Al-18u-260 manufactured by MTI Co., Ltd., substrate thickness: 18 μm) by a doctor blade method (wet film thickness: 100 μm), then dried at 80° C. for 30 minutes, and then dried at 120° C. for 30 minutes to form an active material layer. This was pressure-bonded by a roll pressing machine to produce an electrode C1 (film thickness: 30 μm).

Comparative Example 3-1

0.475 g of lithium iron phosphate (LFP, TATUNG FINE CHEMICALS CO.) as an inorganic active material, 0.352 g of an NMP solution of polyvinylidene fluoride (PVdF) (12 wt %, Kureha Corporation. KF Polymer L #1120) as a binder, 0.0106 g of acetylene black (solid content mass ratio: 90:8.0:2.0) as a conductive auxiliary agent, and 0.255 g of NMP were mixed such that a total solid content concentration was 48 wt %. This was mixed with a planetary centrifugal mixer (3 times at 2,000 rpm for 10 minutes) to prepare an electrode-forming slurry. This was uniformly spread on an aluminum foil (EQ-CC-Al-18u-260 manufactured by MTI Co., Ltd., substrate thickness: 18 μm) by a doctor blade method (wet film thickness: 100 μm), then dried at 80° C. for 30 minutes, and then dried at 120° C. for 30 minutes to form an active material layer. This was pressure-bonded by a roll pressing machine to produce an electrode $C_2$ (film thickness: 30 μm).

Comparative Example 3-21

0.475 g of lithium iron phosphate (LFP, TATUNG FINE CHEMICALS CO.) as an inorganic active material, 0.0525 g of an N-methylpyrrolidone (NMP) solution containing 1 wt % of the polymer PVAQ produced in Comparative Example 1-1, 0.352 g of an NMP solution of polyvinylidene fluoride (PVdF) (12 wt %, Kureha Corporation, KF Polymer L #1120) as a binder, 0.0106 g of acetylene black (solid content mass ratio: 89.9:0.1:8.0:2.0) as a conductive auxiliary agent, and 0.210 g of NMP were mixed such that a total solid content concentration was 48 wt %. This was mixed with a planetary centrifugal mixer (3 times at 2,000 rpm for 10 minutes) to prepare an electrode-forming slurry. This was uniformly spread on an aluminum foil (EQ-CC-Al-18u-260 manufactured by MTI Co., Ltd., substrate thickness: 18 μm) by a doctor blade method (wet film thickness: 100 μm), then dried at 80° C. for 30 minutes, and then dried at 120° C. for 30 minutes to form an active material layer. This was pressure-bonded by a roll pressing machine to produce an electrode $C_3$ (film thickness: 30 μm).

Comparative Example 3-31

0.475 g of lithium iron phosphate (LFP, TATUNG FINE CHEMICALS CO.) as an inorganic active material, 0.0525 g of an N-methylpyrrolidone (NMP) solution containing 1 wt % of PMMA, 0.352 g of an NMP solution of polyvinylidene fluoride (PVdF) (12 wt %, Kureha Corporation, KF Polymer L #1120) as a binder, 0.0106 g of acetylene black (solid content mass ratio: 89.9:0.1:8.0:2.0) as a conductive auxiliary agent, and 0.210 g of NMP were mixed such that a total solid content concentration was 48 wt %. This was mixed with a planetary centrifugal mixer (3 times at 2,000 rpm for 10 minutes) to prepare an electrode-forming slurry. This was uniformly spread on an aluminum foil (EQ-CC-Al-18u-260 manufactured by MTI Co., Ltd., substrate thickness; 18 μm) by a doctor blade method (wet film thickness: 100 μm), then dried at 80° C. for 30 minutes, and then dried at 120° C. for 30 minutes to form an active material layer. This was pressure-bonded by a roll pressing machine to produce an electrode C4 (film thickness: 30 μm).

Comparative Example 3-4

0.475 g of lithium iron phosphate (LFP, TATUNG FINE CHEMICALS CO.) as an inorganic active material, 0.0525 g of an N-methylpyrrolidone (NMP) solution containing 1 wt % of PAN, 0.352 g of an NMP solution of polyvinylidene fluoride (PVdF) (12 wt %. Kureha Corporation, KF Polymer L #1120) as a binder, 0.0106 g of acetylene black (solid content mass ratio: 89.9:0.1:8.0:2.0) as a conductive auxiliary agent, and 0.210 g of NMP were mixed such that a total solid content concentration was 48 wt %. This was mixed with a planetary centrifugal mixer (3 times at 2,000 rpm for 10 minutes) to prepare an electrode-forming slurry. This was uniformly spread on an aluminum foil (EQ-CC-Al-18u-260 manufactured by MTI Co., Ltd., substrate thickness: 18 μm) by a doctor blade method (wet film thickness: 100 μm), then dried at 80° C. for 30 minutes, and then dried at 120° C. for 30 minutes to form an active material layer. This was pressure-bonded by a roll pressing machine to produce an electrode $C_5$ (film thickness: 30 μm).

Example 4-11

The electrode $C_1$ obtained in Example 3-1 was punched into a disk shape having a diameter of 10 mm, and the mass thereof was measured. Then, the disk-shaped electrode was vacuum-dried at 100° C. for 15 hours, and transferred to a glove box filled with argon.

A lithium foil (manufactured by Honjo Chemical Corporation, thickness: 1.0 mm) punched out to a diameter of 15 mm was set on a 2032 coin cell (manufactured by Hohsen Corporation) cap to which a washer and a spacer had been welded. One separator (2400 manufactured by Celgard KK) punched out to a diameter of 16 mm which had been impregnated for at least 24 hours with an electrolyte solution (manufactured by Kishida Chemical Co., Ltd.; an ethylene carbonate:diethyl carbonate=3:7 (volume ratio) solution containing 1 mol/L of lithium hexafluorophosphate as the electrolyte) was stacked thereon. Furthermore, an electrode was stacked on top with the active material layer-formed surface facing down. A single drop of electrolyte solution was dropped thereon, and a case and a gasket were then placed thereon, followed by carrying out sealing with a coin cell crimper. The cell was then allowed to stand for 24 hours to obtain a secondary battery for testing.

Comparative Examples 4-1 to 4-4

Secondary batteries for testing were prepared in the same manner as in Example 4-1 except that the electrodes C2 to C5 prepared in Comparative Examples 3-1 to 3-4 were used instead of the electrode C1.

For the lithium ion secondary batteries produced in Example 4-1 and Comparative Examples 4-1 to 4-4, the physical properties of the electrodes were evaluated under the following conditions using a charge/discharge measurement apparatus. A discharge voltage and a discharge capacity at a discharge rate during 10 C discharge of each secondary battery are shown in Table 1.

[Measurement Conditions]
Rate Characteristics: Current: 0.5 C constant current charge, 10 C constant current discharge (capacity of LFP was set to 152 mAh/g)
Cut off voltage: 4.20 V to 2.00 V
Temperature: room temperature For the lithium ion secondary batteries produced in Example 4-1 and Comparative Examples 4-1 to 4-4, the physical properties of the electrodes were evaluated under the following conditions using a charge/discharge measurement apparatus. A charge voltage and a charge capacity at a charge rate during 10 C charge of each secondary battery are shown in Table 2.

[Measurement Conditions]
Rate Characteristics: Current: 10 C constant current charge, 0.5 C constant current discharge (capacity of LFP was set to 152 mAh/g)
Cut off voltage: 4.20 V to 2.00 V
Temperature: room temperature

TABLE 1

| | Electrode | Material | Amount of addition [wt %] | Discharge voltage at 10 C [V] | Discharge capacity at 10 C [mAh/g] |
|---|---|---|---|---|---|
| Example 4-1 | C1 | Polymer A | 0.1 | 2.99 | 111.9 |
| Comparative Example 4-1 | C2 | Additive-free | 0 | 2.90 | 105.4 |
| Comparative Example 4-2 | C3 | PVAQ | 0.1 | 2.85 | 98.9 |
| Comparative Example 4-3 | C4 | PMMA | 0.1 | 2.93 | 99.4 |
| Comparative Example 4-4 | C5 | PAN | 0.1 | 2.88 | 103.0 |

TABLE 2

| | Electrode | Material | Amount of addition [wt %] | Charge voltage at 10 C [V] | Charge capacity at 10 C [mAh/g] |
|---|---|---|---|---|---|
| Example 4-1 | C1 | Polymer A | 0.1 | 3.69 | 141.6 |
| Comparative Example 4-1 | C2 | Additive-free | 0 | 3.72 | 139.9 |
| Comparative Example 4-2 | C3 | PVAQ | 0.1 | 3.73 | 137.1 |
| Comparative Example 4-3 | C4 | PMMA | 0.1 | 3.73 | 136.9 |
| Comparative Example 4-4 | C5 | PAN | 0.1 | 3.71 | 137.6 |

From the results of Tables 1 and 2, a battery having excellent rate characteristics was confirmed to be obtained by using the electrode material containing the fluoflavine skeleton-containing polymer defined in the present invention.

The invention claimed is:

1. An electrode material comprising:
a polymer having a fluoflavine skeleton in a side chain; and
an inorganic active material,
wherein the polymer is contained in an amount of 1 wt % or less in a solid content.

2. The electrode material according to claim 1, wherein the polymer is a polymer containing a repeating unit having the following formula (1):

[Chem. 1]

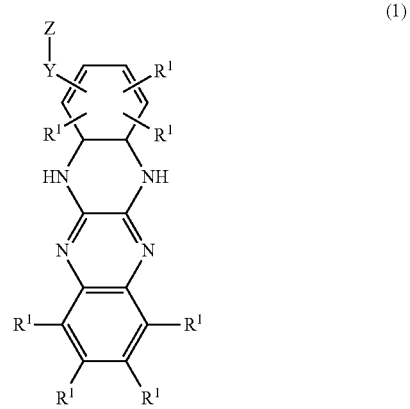

(1)

wherein Z represents a partial structure having the following formula (Z-1), (Z-2), or (Z-3)

[Chem. 2]

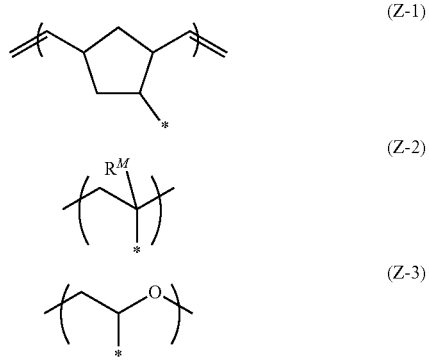

(Z-1)

(Z-2)

(Z-3)

wherein:
RM represents a hydrogen atom or a methyl group;
Y represents a single bond, —O—, —CO—, —COO—, —OCO—, —CH2-, —NH—, —NCH3-, —NHCO—, —CONH—, —CH2NHCO—, —CONHCH2-, or —S—;
R1s each independently represent a hydrogen atom, a halogen atom, a hydroxyl group, a carboxy group, an alkyl group having 1 to 10 carbon atoms which may be substituted with a halogen atom, an alkoxy group having 1 to 10 carbon atoms which may be substituted with a halogen atom, or an aryl group having 6 to 12 carbon atoms which may be substituted with a halogen atom; and
* represents a bonding site.

3. The electrode material according to claim 2, wherein the Z is a partial structure having formula (Z-1).

4. The electrode material according to claim 1, wherein all of the R1s are hydrogen atoms.

5. The electrode material according to claim 1, wherein the Y is a single bond.

6. The electrode material according to claim 5, wherein the inorganic active material is at least one selected from a metal, a metalloid, a metal alloy, a metal oxide, a metalloid oxide, a metal phosphate, a metal sulfide, and a metal nitride.

7. The electrode material according to claim 1, further comprising a solvent.

8. The electrode material according to claim 1, further comprising a conductive auxiliary agent and a binder.

9. An electrode comprising an active material layer made of the electrode material according to claim 1.

10. A secondary battery comprising the electrode according to claim 9.

11. A polymer comprising a repeating unit having the following formula (1):

[Chem. 3]

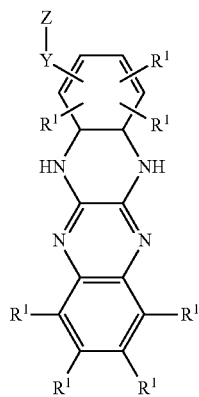

(1)

wherein Z represents a partial structure having the following formula (Z-1), (Z-2), or (Z-3)

[Chem. 4]

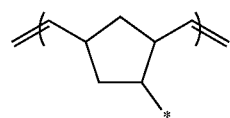 (Z-1)

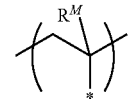 (Z-2)

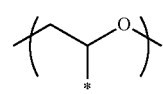 (Z-3)

wherein:
RM represents a hydrogen atom or a methyl group,
Y represents a single bond, —O—, —CO—, —COO—, —OCO—, —CH2-, —NH—, —NCH3-, —NHCO—, —CONH—, —CH2NHCO—, —CONHCH2-, or —S—, provided that when Z is the partial structure having formula (Z-1), Y is not —CH2NHCO—, and when Z is the partial structure having formula (Z-2), Y is not a single bond;
R1s each independently represent a hydrogen atom, a halogen atom, a hydroxyl group, a carboxy group, an alkyl group having 1 to 10 carbon atoms which may be substituted with a halogen atom, an alkoxy group having 1 to 10 carbon atoms which may be substituted with a halogen atom, or an aryl group having 6 to 12 carbon atoms which may be substituted with a halogen atom; and
* represents a bonding site.

12. The polymer according to claim 11, wherein the Z is a partial structure having formula (Z-1).

13. The polymer according to claim 11, wherein all of the R1s are hydrogen atoms.

14. The polymer according to claim 11, wherein the Y is a single bond.

* * * * *